United States Patent [19]

Delon-Martin et al.

[11] Patent Number: 5,197,019

[45] Date of Patent: Mar. 23, 1993

[54] METHOD OF MEASURING DISTANCE USING ULTRASONIC WAVES

[75] Inventors: Chantal Delon-Martin, Grenoble, France; marcel Arditi, Genève, Switzerland; Pierre-André Farine, Neuchâtel, Switzerland; Jean-Jacques Meister, Epalinges, Switzerland; Yanik Tardy, Lausanne, Switzerland

[73] Assignee: Asulab S.A., Bienne, Switzerland

[21] Appl. No.: 554,420

[22] Filed: Jul. 19, 1990

[30] Foreign Application Priority Data

Jul. 20, 1989 [FR] France .................... 89 09926

[51] Int. Cl.⁵ .................... G01B 17/00; G06F 15/42
[52] U.S. Cl. .................... 364/563; 364/413.25; 73/602
[58] Field of Search .............. 364/561, 563; 73/597, 73/602, 622

[56] References Cited

U.S. PATENT DOCUMENTS

| | | | |
|---|---|---|---|
| 4,049,954 | 9/1977 | Da Costa Vieira | 235/151.32 |
| 4,063,549 | 12/1977 | Beretsky | 128/2 |
| 4,534,220 | 8/1985 | Kleeper | 73/599 |
| 4,648,276 | 3/1987 | Klepper | 73/599 |
| 4,799,177 | 1/1989 | Sarr | 364/563 |
| 4,817,432 | 4/1989 | Wallace et al. | 73/602 |
| 4,855,911 | 8/1989 | Lele et al. | 73/602 X |
| 4,926,870 | 5/1990 | Brandenburger | 73/597 X |
| 5,000,183 | 3/1991 | Bonnefous | 73/602 X |
| 5,038,615 | 8/1991 | Trulson et al. | 73/597 |
| 5,050,226 | 9/1991 | Collet-Billon | 73/602 X |

OTHER PUBLICATIONS

Ultrasonic Imaging 6, 435-451 (1984); Range Resolution Improvement by a Fast Deconvolution Method; G. Demoment.

Measurement of the Thickness of Thin Layers by Ultrasonic Interferometry M. Houze; Jul. 19, 1983; pp. 194-198.

Digital Signal Processing Method for Multilayered Media Thickness Measurement C. Delebarre; 1988 Ultrasonics Symposium pp. 1027-1029.

Primary Examiner—Parshotam S. Lall
Assistant Examiner—Michael Zanelli
Attorney, Agent, or Firm—Griffin Butler Whisenhunt & Kurtossy

[57] ABSTRACT

A method for measuring the distance e separating two faces (3, 4) of an object (1) employs the ultrasonic wave diffused back by said faces and received by a sensor (6). Following digitalization (11), the temporal signal is transformed (12) into a frequency spectrum. The modulus of the frequency spectrum is established (13) then the logarithmic derivative thereof is calculated (15) from whence there results a useful signal including a periodic signal onto which a linear signal is superposed. Following suppression (14, 16) of the linear signal the useful signal is applied (17) to a frequency window in order to eliminate the noise therefrom. The signal thus obtained is inversely transformed (18) to obtain a signal the amplitude of which is a function of the time and the envelope of this latter signal is determined (19). After having determined the temporal spread $\Delta t$ separating the time origin from the envelope peak showing the greatest amplitude, the distance e is calculated from the relation $e = c \cdot \Delta t / 2$, c representing the propagation velocity of the ultrasonic wave. The method may be employed for the non-invasive measurement of the thickness or diameter of an artery or indeed for the measurement of the thickness of thin layers.

16 Claims, 8 Drawing Sheets

METHOD OF MEASURING DISTANCE USING ULTRASONIC WAVES

FIELD OF THE INVENTION

The present invention relates to a method for measuring the distance e separating two faces of an object, such method including the emitting of an ultrasonic wave propagating at the velocity c in the direction of the object and the reception by a sensor of the echoes generated by reflection of the wave from the faces of the object, the sensor delivering a composite electrical signal g(t) exhibiting an amplitude varying as a function of the time.

BACKGROUND OF THE INVENTION

Several methods have already been proposed which employ the ultrasonic way in order to measure the distance separating two faces of an object. If the distance separating the two faces is substantial, there is in general no difficulty in interpreting the double signal received in the form of an echo since the faces generate two peaks which are clearly separated in time and which permit, knowing the speed of propagation of the wave in the medium in which it is propagated, calculation of the distance which separates the faces in question. However, when the faces are very close to one another and spaced a distance on the order of the wave length from one another, the echoes which they produce may appear merged.

Coating thicknesses applied to a substrate which thicknesses comprise between 5 and 20 $\mu m$, have been apt to be measured by ultrasonic interferometry employing a frequency varying from 90 to 510 MHz. Such a method is described in the article entitled "Measurement of the Thickness of Thin Layers by Ultrasonic Interferometry" appearing in J. Appl. Phys. 55 (1), January, 1984, pages 194-198. However, this method furnishes a satisfactory result only if it is applied to a stable object, the dimensions of which are not subject to variations during the measurement.

The article entitled "Digital Signal Processing Method for Multilayered Media Thickness Measurement" which appeared in IEEE Ultrasonic Symposium 1988, pages 1027-1029, describes an ultrasonic measurement carried out on thin layers of paint applied in the automobile industry. In this case the layers exhibit thicknesses between 20 and 110 $\mu m$. The central frequency here is around 75 MHz with a band width of 100 MHz. The measurement method is based on the analysis of a power cepstrum, defined as being the inverse Fourier transformation of the logarithm of the power spectral density of the radio frequency signal. Here however one is in the presence of superficial layers which permit working at a high frequency from whence derives a result enabling good resolution. This method is not suitable for the measurement of the thickness of an object situated within a medium attenuating the ultrasonic wave and which would thus oblige working at lower frequencies (10 MHz) as will be the case in a possible employment of this invention.

The cepstrum method is likewise the object of a thesis presented Feb. 9, 1979 at the National Polytechnical Institute of Grenoble by J. C. Balluet, which thesis is entitled "Les opérateurs cepstres, applications à la séparation d'échos rapprochés". In this publication it will be noted however that the method employed for echoes which are very close to one another gives results which are difficult to interpret and that the observed peaks are located at the limit of visibility.

An ultrasonic echography method applied in vivo on living tissues is described in the article entitled "Range Resolution Improvement by a Fast Deconvolution Method", which appeared in Ultrasonic Imaging 6, 1984, pages 435-451. Numerous problems of mathematical physics may be formulated by means of an equation of convolution of the form y=h*x, where x and y denote a system of input and output respectively and where h is the pulse response of the system. The deconvolution is the inverse problem which consists in reconstructing the input on the basis of an output measured experimentally. Thanks to the method set forth in this article, it has been possible to study with precision the bottom of the eye and to follow the variations of the thickness of an arterial wall during the cardiac cycle. The method proposed however presents the disadvantage of separating only with great difficulty echoes which are very close in time.

Non-invasive sensors enabling the measurement of the interior diameter of an artery are known from U.S. Pat. No. 4,370,985 granted to Takeichi on Feb. 1, 1983. The indicated method gives no solution for measuring the actual thickness of the artery.

SUMMARY OF THE INVENTION

From the contents of the literature briefly set forth hereinabove, it is apparent that the methods employed either are poorly adapted to the medium in which the measurement must be effected, or give results which are difficult to interpret when it concerns measurement of very small thicknesses. To overcome these difficulties, the present invention is characterized by the fact that the composite electrical signal received by the sensor is subjected to a processing which includes the following sequence of steps:

a) one transforms the composite electrical signal g(t) coming from the sensor into a frequency spectrum G(f) the amplitude of which is a function of the frequency, said spectrum exhibiting a real part Re[G(f)] and an imaginary part Im[G(f)], b) one calculates the order n modulus of the frequency spectrum $|G(f)|^n = \{Re[G(f)]^2 + Im[G(f)]^2\}^{n/2}$, c) one calculates the logarithmic derivative $(|G(f)|^n)'/|G(f)|^n$ of the modulus calculated in step b) in order to separate the existing echoes from the composite electrical signal, said logarithmic derivative exhibiting a useful part centered substantially on the frequency of the ultrasonic wave and a part having noise located on either side of the useful part, said useful part comprising a periodic signal onto which a substantially linear signal is superposed, d) one applies a frequency window to the logarithmic derivative in order to isolate the useful part thereof and to eliminate the part having noise, e) one applies a transformation inverse to that of step a), at least to the periodic signal of said useful part, f) one determines the envelope of the inverse transformation, said envelope exhibiting a series of variable amplitude peaks spaced out over time, g) one determines the temporal spread $\Delta t$ separating the time origin from the peak showing the greatest amplitude due to the contribution of the periodic signal from the useful part, the sought for distance e separating the two faces of the object being expressed by the relation $e = c \cdot \Delta t / 2$.

The invention will now be understood from reading the following description given by way of example and illustrated by the drawings.

DESCRIPTION OF THE PREFERRED EMBODIMENT

Figure 1:
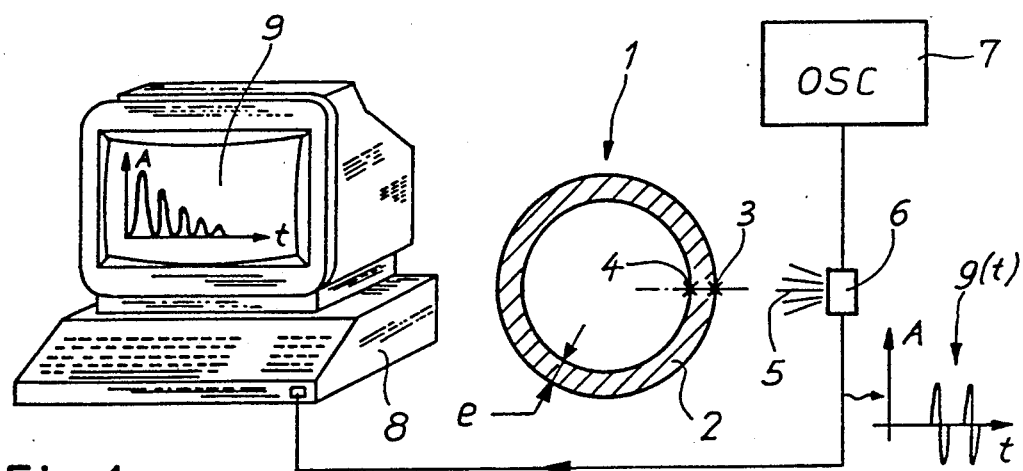
FIG. 1 is a schematic view of an example of the measurement arrangement showing an object for which it is desired to measure the thickness of the wall, and a sensor delivering a composite electrical signal to a computer, this signal undergoing the processing which is the object of this invention.

FIG. 1 shows in cross-section an object 1 for which the thickness of the wall 2 is to be measured. The wall is bounded by an external face 3 and an internal face 4. In order to proceed with this measurement, there is emitted an ultrasonic wave 5 by means of an ultrasonic sensor emitter-receiver 6, each wave being propagated at velocity c in the direction of the object. In emission, the sensor is excited by an oscillator 7, the frequency of which is on the order of 10 MHz. In the example, sensor 6 likewise serves as a receiver of the echoes generated by reflection of the wave from the faces 3 and 4 of the object. This sensor delivers a composite electrical signal g(t) which exhibits an amplitude A varying as a function of time t. This electrical signal is subjected to processing according to a method which is the object of this invention. All the processing may be carried out by means of a personal computer (PC) represented at 8 on FIG. 1.

At each step of the method it is possible by means of display 9 to visualize the calculation effected. It will be here mentioned that the entire method according to the invention may be carried out by an IBM AT personal computer to which there is added a type 8087 mathematical coprocessor. Other apparatus could be employed, those which have just been indicated constituting only one possible example.

Figure 2:
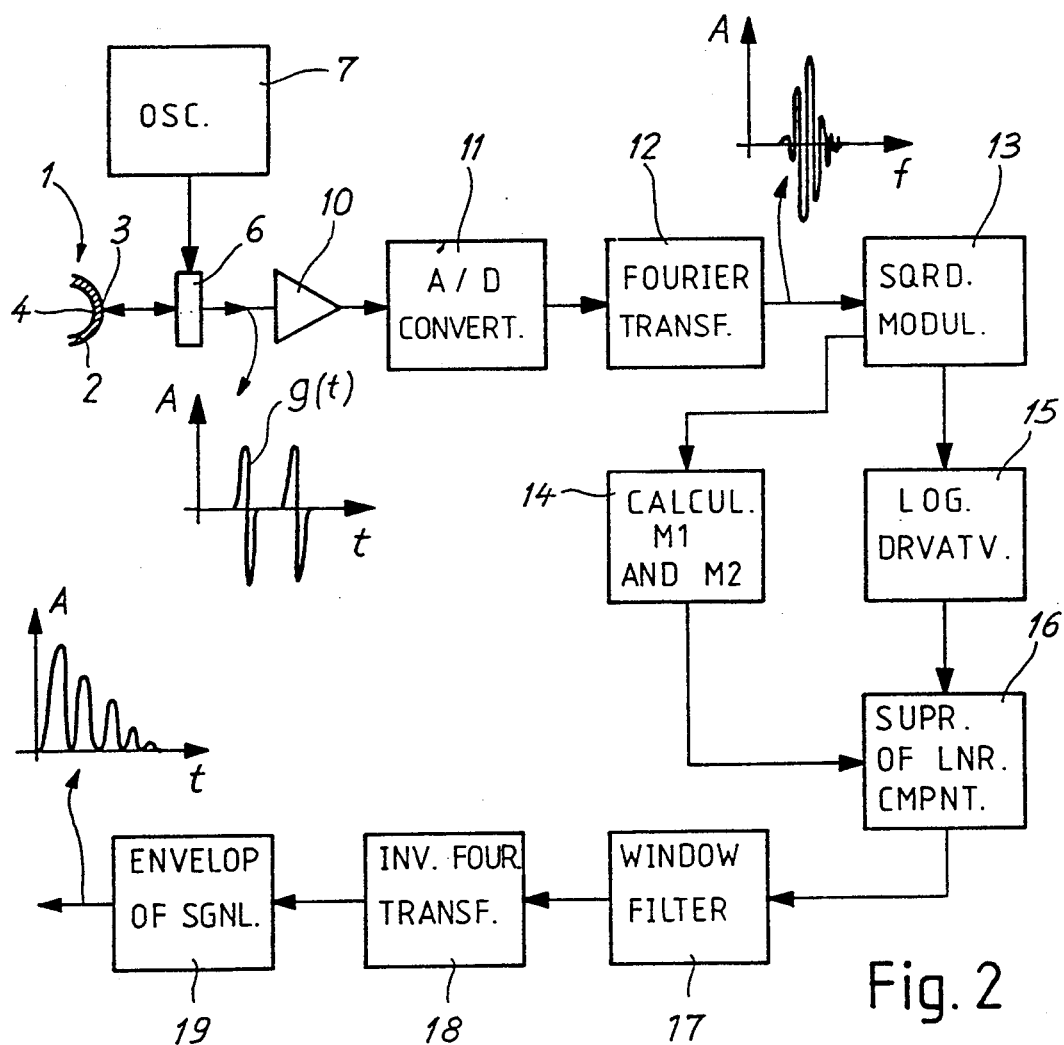
FIG. 2 is a flow chart showing the state of the various steps of the method according to the invention and according to one example of processing of the signal.

The flow chart of FIG. 2 shows different blocks which each illustrate one operation of the method. The disposition here shown is that which is the most complete. The description which is to follow will however indicate that certain blocks can be eliminated without straying however from the principal idea of the invention.

Oscillator 7 excites a piezoelectric sensor 6 which emits an ultrasonic wave having a central frequency of about 10 MHz. This same sensor gathers in the signal g(t) diffused back by faces 3 and 4 of wall 2 of object 1. This signal exhibits an amplitude A varying as a function of the time t and is presented in an analog form at the output of sensor 6. Following amplification in the amplifier 10 it is convenient, but not absolutely necessary, to digitize the signal g(t) by means of an analog-digital converter 11. In the case taken here as example, the signal is sampled at 100 MHz over 8 bits, then stored in a memory including 2048 points.

The object employed here in order to explain the method of the invention is a tube of plastic material for which one proposes to measure the thickness of the wall. As one can measure this thickness by other well known means as for example by means of a micrometer, one will be able to confront the results of the measurement of the two systems which will permit verifying the results obtained according to the method of the invention.

Figure 3:
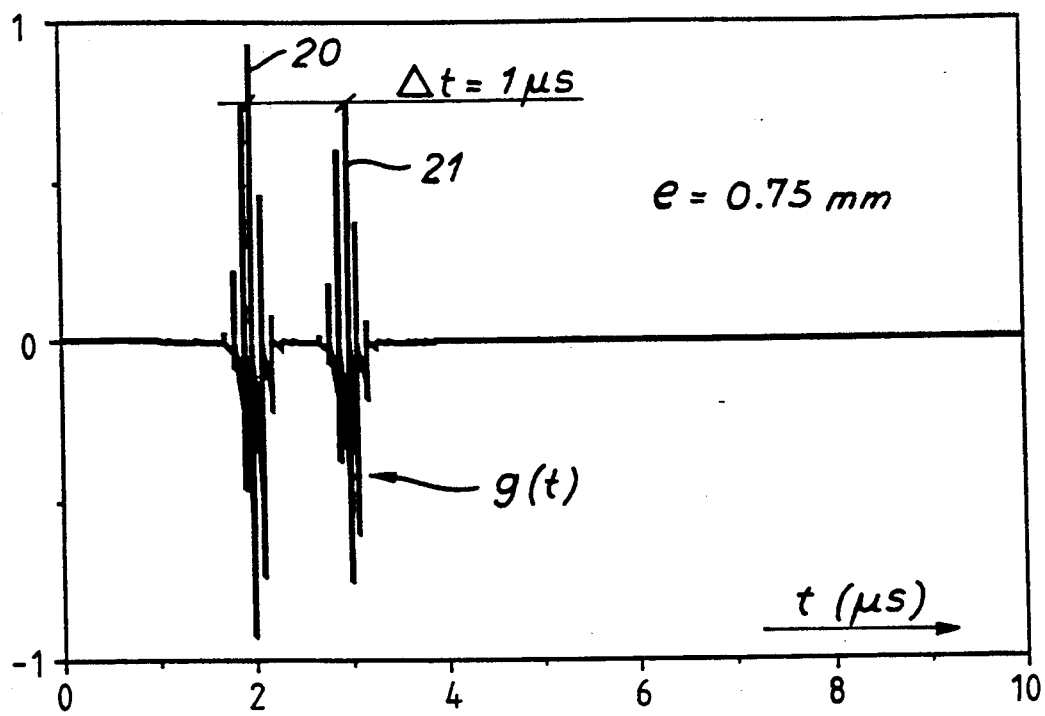
FIG. 3 shows the composite signal delivered by the sensor when the thickness of the wall is on the order 0.75 mm, the wall being here that of a tube of plastic material.
Figure 4:
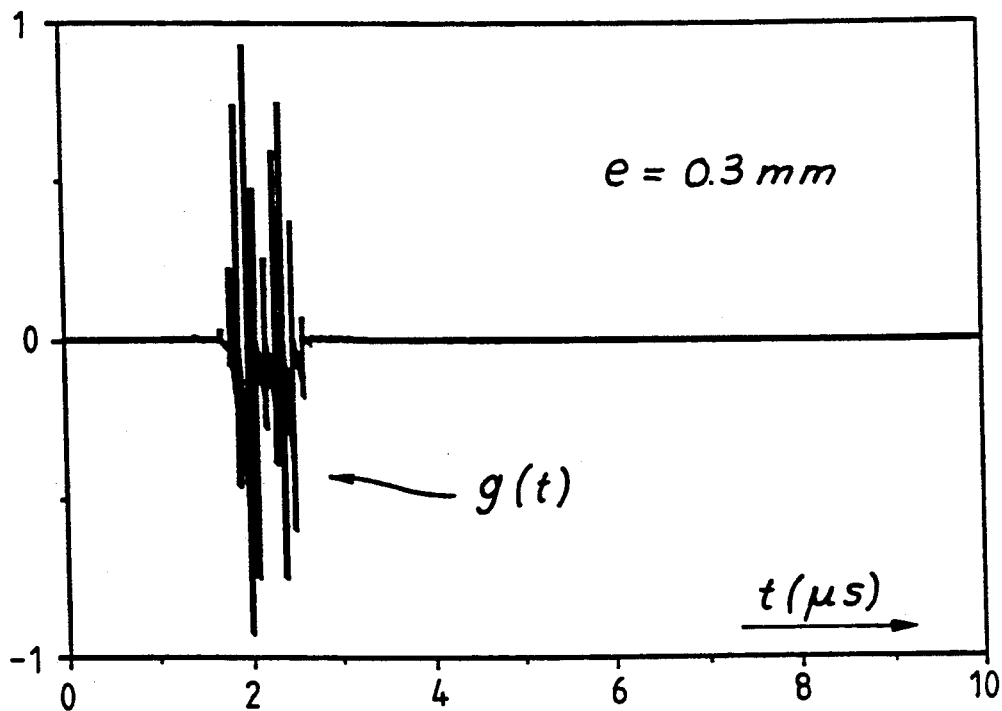
FIG. 4 shows the same signal for a thickness of 0.3 mm.
Figure 5:
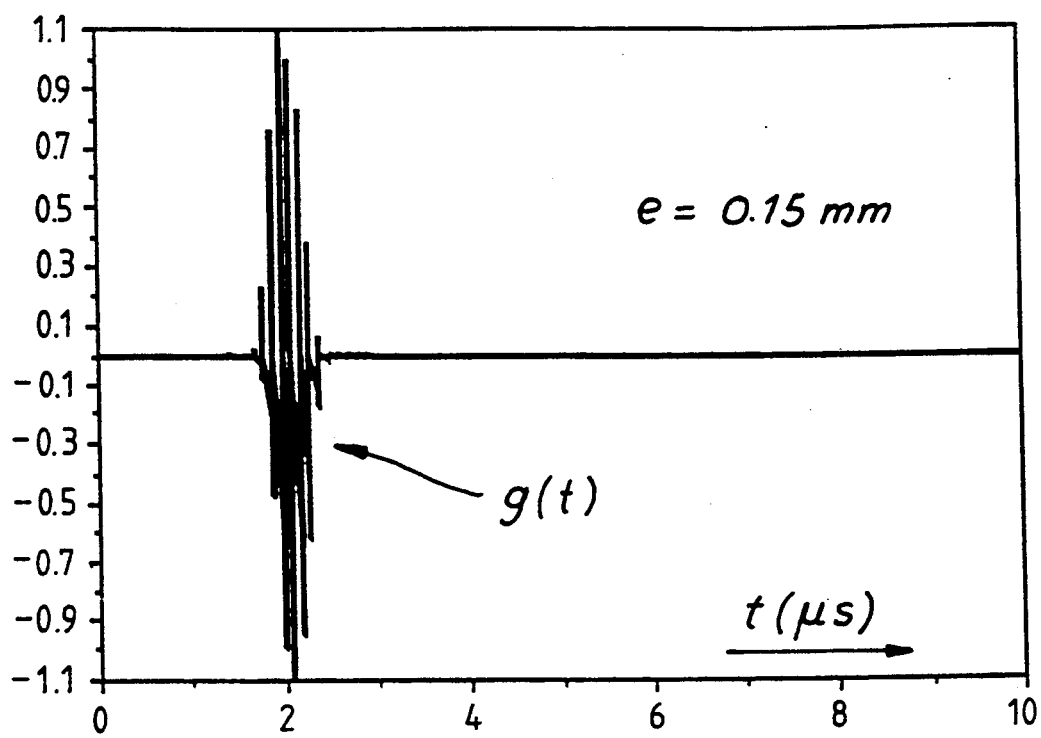
FIG. 5 shows the same signal for a thickness of 0.15 mm.
Figure 6:
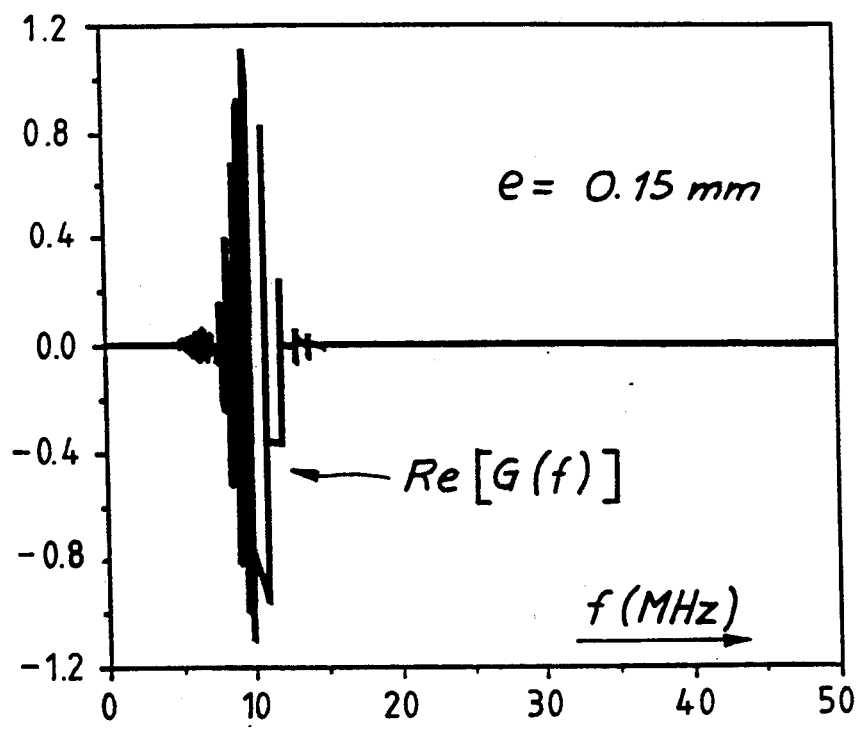
FIG. 6 is a diagram showing the real part of the frequency spectrum obtained in transforming the signal issuing from the sensor for the signal of FIG. 5.
Figure 7:
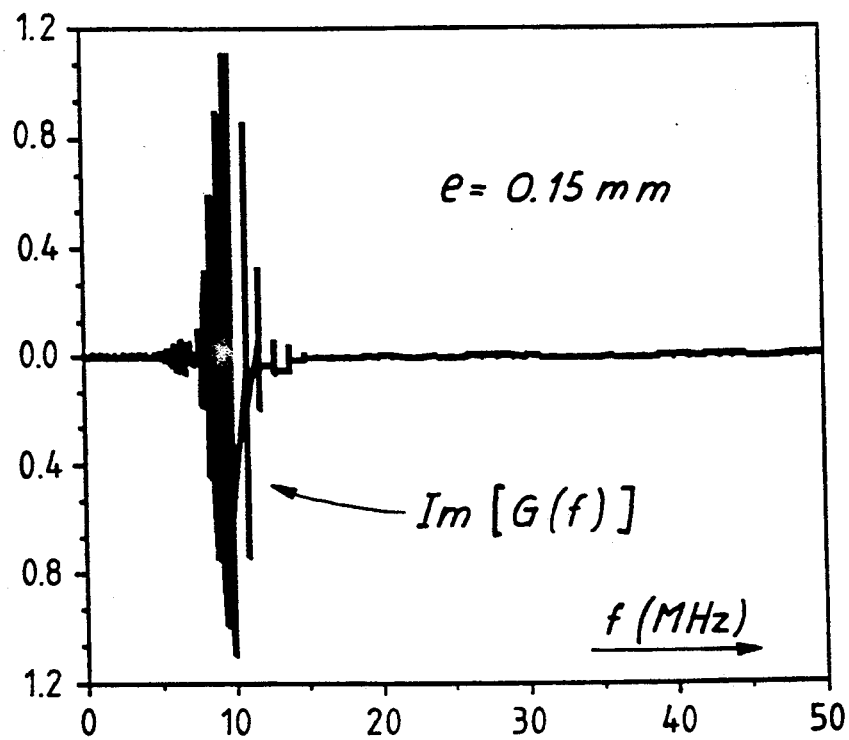
FIG. 7 shows the imaginary part of the frequency spectrum obtained in transforming the signal issuing from the sensor for the signal of FIG. 5.
Figure 8:
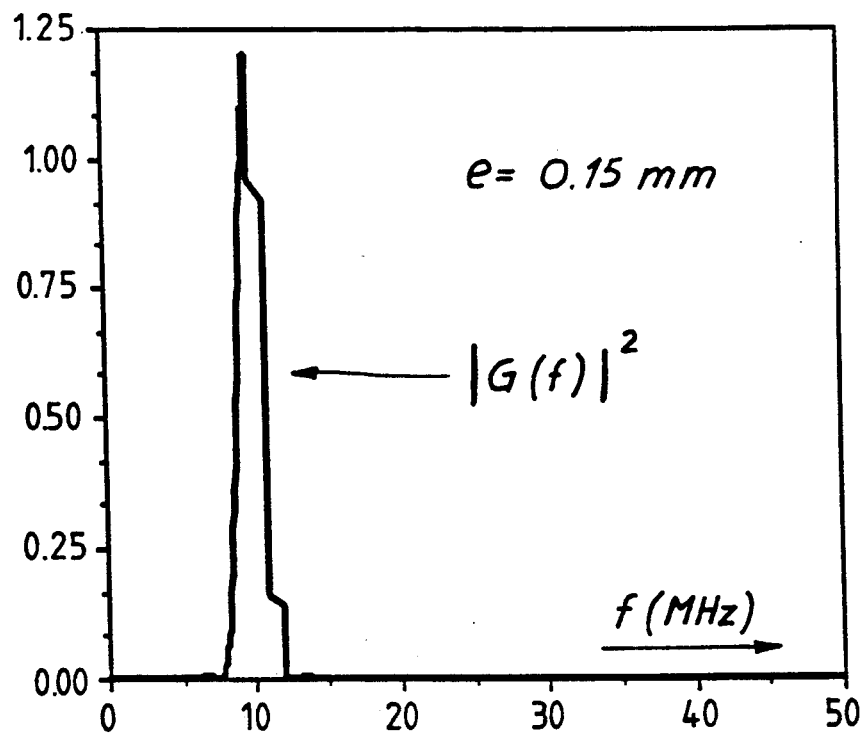
FIG. 8 is a diagram showing the squared modulus of the frequency spectrum shown on FIGS. 6 and 7.

The diagrams of FIGS. 3, 4 and 5 each show the signal g(t) following digitizing and for three particular cases of the thickness of the tube wall. In these diagrams, there has been indicated the amplitude of the signal on the ordinate (relative value) and the time on the abscissa (value given in microseconds).

FIG. 3 shows the signal g(t) for a wall thickness e=0.75 mm. Here one clearly distinguishes the two echoes 20 and 21 sent back by the exterior face 3 and interior face 4 of the wall. If one measures the time $\Delta t$ on the diagram separating the two main peaks of the signal, one finds $\Delta t = 1$ s. Since one furthermore knows the velocity c of wave propagation which is equal in the particular case taken as example, to 1.5 mm/$\mu$s, one may immediately calculate the thickness of the wall which is equal to $e = c \cdot \Delta t / 2$, the division by 2 taking into account the sending and return of the wave. By replacing c and $\Delta t$ in the formula by 1.5 and 1 respectively, one will find for the thickness e the value of 0.75 mm. One determines that in the case where echoes are clearly separated, the measure of the thickness is immediate and that it is not necessary to appeal to a method according to the invention.

FIG. 4 shows the signal g(t) for a wall thickness of 0.3 mm. Here the two echoes are closer together and if one proceeds with the same operation as previously, one will be able to obtain a result corresponding more or less to reality according to the peaks which one will have chosen.

FIG. 5 shows the signal g(t) for a wall thickness of 0.15 mm. Here the two peaks to be chosen are difficult, indeed impossible to determine. The echoes appear as merged and it is the purpose of this invention to propose a calculation method capable of isolating the peaks to be taken into consideration in order to measure the thickness of the wall. This method is now going to be applied to the case of the tube giving as initial signal g(t) that represented on FIG. 5. For this we will refer back to FIG. 2 as well as to the series of diagrams shown in FIGS. 5 to 13.

Exposition of the Method a) The composite electrical signal g(t) present at the output of block 11 and represented on FIG. 5 initially undergoes an operation in block 12, this operation consisting in transforming said signal depending from time into a frequency spectrum, the amplitude A of which depends on the frequency f. This operation is generally preceded by an offset correction in the case where the signal g(t) is provided therewith. In a completely general manner, it may concern here a transformation in z introduced by Hurewiez for the study of servomechanisms. On this subject reference may be had to the work entitled "Theory of Servomechanisms" published by McGraw-Hill Book Co., Inc. New York, chapter 5, 1947. In the case which here interests us, there will be used to advantage a special case of the z transformation which is the well known Fourier transformation. Following transformation, and at the output of block 12, the signal G(f) appears in the form of a real part Re[G(f)] shown on FIG. 6 and an imaginary part Im[G(f)] shown on FIG. 7.

b) The two parts, real and imaginary, of the frequency spectrum G(f) are then introduced into block 13 (FIG. 2), the purpose of which is to calculate the n order modulus of said spectrum according to the relation $|G(f)|^n = \{Re[G(f)]^2 + Im[G(f)]^2\}^{n/2}$. In the special case, one will employ to advantage the squared modulus of the frequency spectrum by making n=2. This squared modulus is represented on FIG. 8 which shows a very pronounced peak over the central emission frequency of the ultrasonic sensor (about 10 MHz).

c) The modulus obtained at the output of block 13 is then introduced into block 15 (FIG. 2) the role of which is the calculation of the logarithmic derivative of the modulus defined by the quotient of the derivative of the modulus $(|G(f)|^n)'$ over the actual modulus $|G(f)|^n$. There it concerns the most important step of the invention thanks to which it will be possible to separate the composite electrical signal from the two echoes which are sought after. At the output of block 15, the logarithmic derivative appears in the form represented on FIG. 9 which shows distinctly two parts: a useful part 25, substantially centered on the ultrasonic wave frequency, and a noise portion 26 situated on either side of the useful part. The useful part 25 which is the interesting part, comprises a periodic signal 27 onto which is superposed a substantially linear signal 28. These two components of the useful part are physically explained: the starting signal g(t) includes in effect a double peak to be detected, this double peak being mixed with the signal emitted by the sensor which may be assimilated to a sinusoidal signal modulated in amplitude by a gaussian. The Fourier transformation G(f) of the signal g(t) further shows a mixture and when one calculates therefrom the logarithmic derivative, the peaks are transformed into a periodic signal 27 and the signal emitted by the sensor into a substantially linear signal 28. It will here be noted that this separation is easily obtainable in the frequency domain, while not being possible in the time domain which explains the transformation carried out in step a).

In a preferred but not essential version of the invention, one then suppresses the linear signal 28 which is present on diagram 9 in the form of a slope. The suppression of this slope gives an advantage which will appear subsequently. Several methods may be employed in order to suppress this slope or linear signal, these methods giving rise to a signal represented on FIG. 10 and referenced $G_1(f)$.

Figure 9:
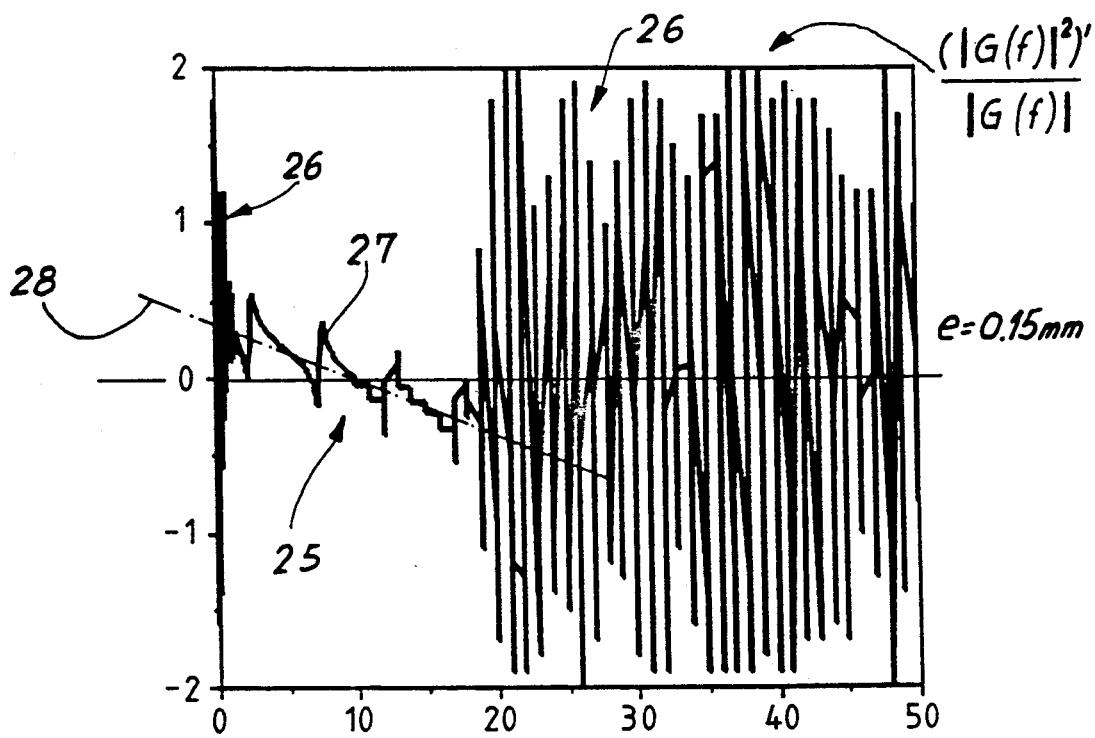
FIG. 9 is a diagram showing the logarithmic derivative of the squared modulus shown on FIG. 8.
Figure 10:
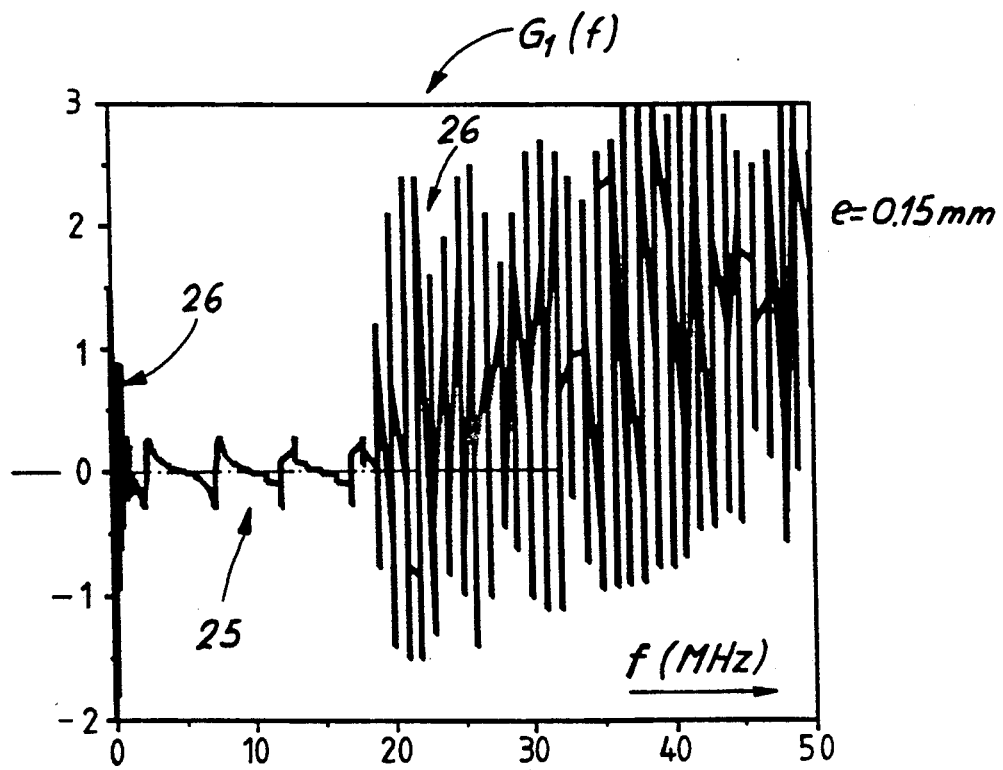
FIG. 10 is a diagram similar to that of FIG. 9 in which a curve adjustment has been carried out.

A first method consists in visualizing on a screen the signal represented on FIG. 9, then proceeding with the suppression of the linear signal in rectifying this signal by means of trials or successive approximations until one obtains a graphically satisfactory result of the type shown on FIG. 10. This will be the case when the slope 28 will have been merged with the frequency axis. Such operation is symbolized by block 16 on FIG. 2.

A second method employs a mathematical way. One begins by calculating from the expression of the squared modulus (n=2) obtained following step b), the moment m1 of order 1 and the moment m2 of order 2 of said modulus. These moments are given by the following relation in making n=1 for m1 and n=2 for m2:

$$m_n = \frac{\sum_{i=-\infty}^{i=+\infty} |G(f)|^2 \cdot f^n}{\sum_{i=-\infty}^{i=+\infty} |G(f)|^2}$$

One next determines the straight line passing by f=m1 and having for slope p=k·m2, which straight line is expressed by the relationship p(f−m1), where f is equal to the frequency and k is a constant. Finally, one subtracts the straight line defined hereinabove from the logarithmic derivative obtained in step c) in a manner to obtain:

$$G_1(f) = (|G(f)|^2)'/|G(f)|^2 - p(f-m1)$$

In the flow chart of FIG. 2, block 14 represents the calculation of moments m1 and m2 of the modulus obtained at block 13 and block 16 represents the actual suppression of the slope or linear signal which is brought about by the subtraction indicated hereinabove.

Figure 11:
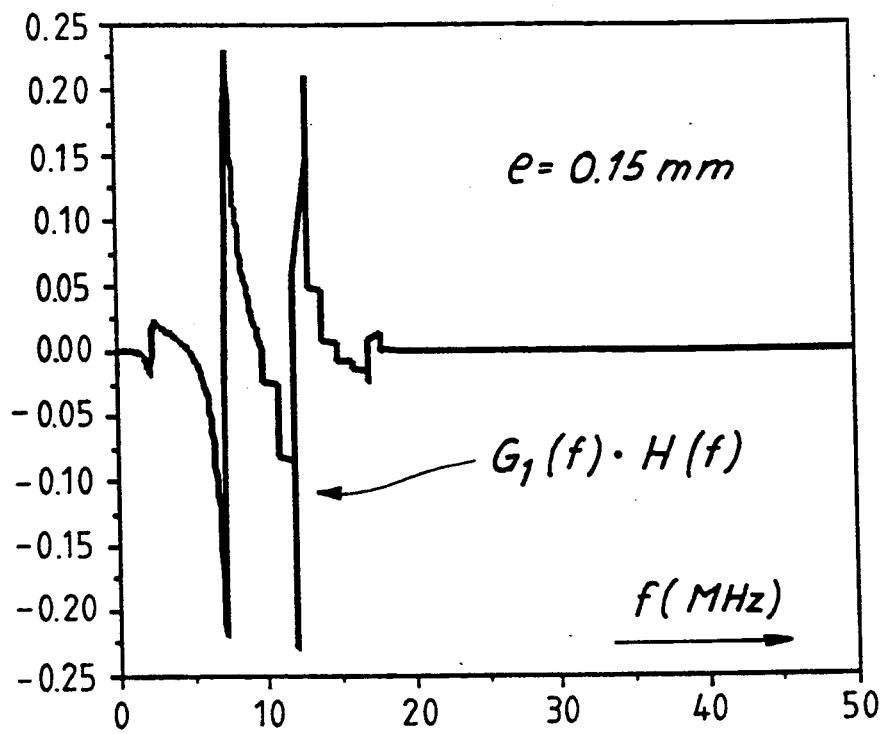
FIG. 11 is a diagram showing the signal of FIG. 10 after having applied thereto a frequency window.
Figure 12:
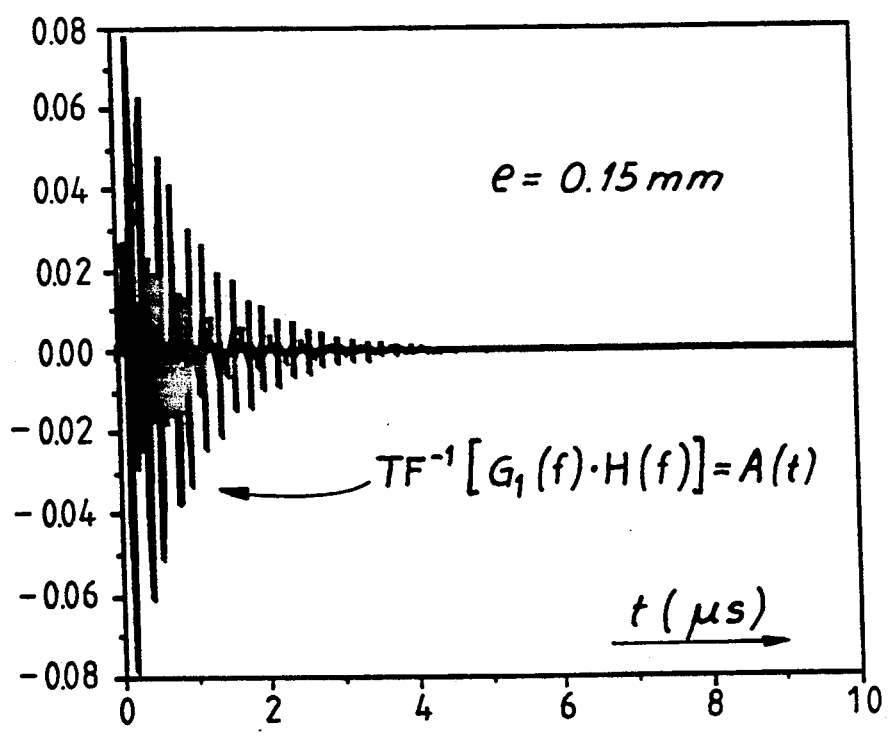
FIG. 12 is a representation of the inverse transformation of the signal of FIG. 11.
Figure 13:
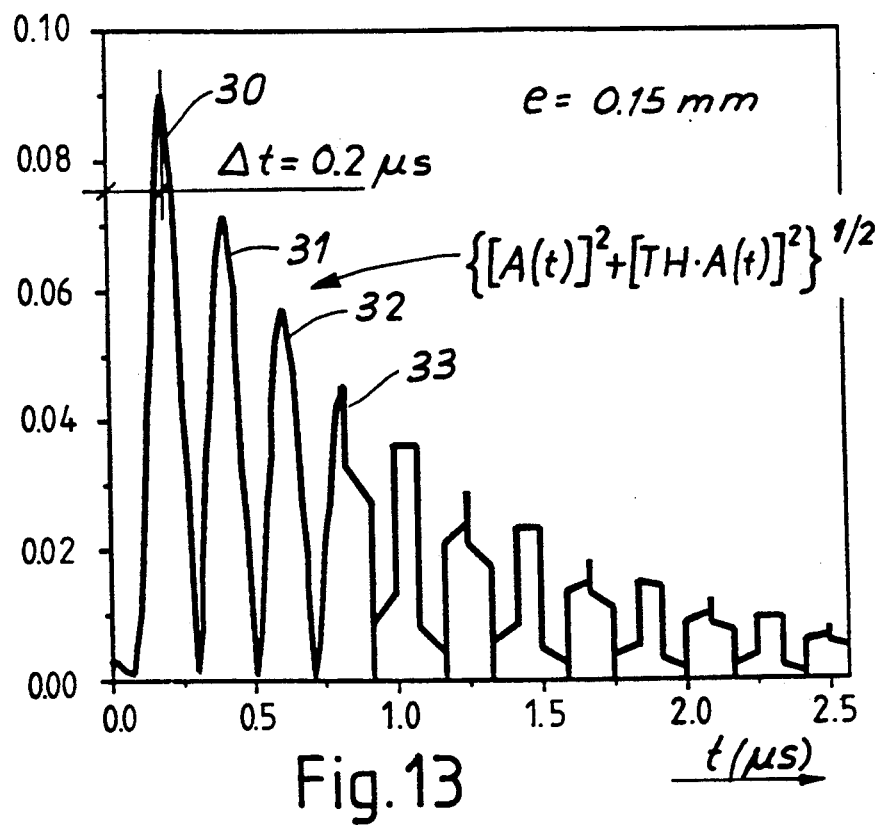
FIG. 13 is a diagram where there has been represented the envelope of the signal of FIG. 12 with an expanded abscissa scale, which envelope enables calculating the thickness of the tube wall.

A third method employs the characteristics of the substantially linear part known a priori by a reference measurement.

d) To the logarithmic derivative obtained in step c), one applies a frequency window in order to isolate the useful part 25 and to eliminate the noise part 26. This operation takes place immediately following step c) represented by block 15 in the case where one does not proceed to correction of the slope suggested hereinabove. In the case where the correction of the slope is effected (block 16), the frequency window may be applied indifferently before or after this correction. In the flow chart of FIG. 2 which provides a slope correction, one opted for application of the window (block 17 of FIG. 2) after said correction (block 16) and the diagram of FIG. 11 shows the signal following application of the window. This window is a band-pass filter which, as is shown on FIG. 11, causes the disappearance of the noise part which is located on either side of the useful part. Advantageously, the window shows a bell form of the type of window called Hanning (see the work entitled "The Measurement of Power Spectra" by R. B. Blackman and J. W. Tuckey, Dover Publications New York 1958). Other windows may be employed and for this one may consult the work of M. Kunt entitled "Traitement numérique des signaux" published by Dunod, 1981.

e) The signal following the window is rendered usable if one returns now into the time domain which is effected by block 18 on FIG. 2, which applies to the signal a transformation inverse to that which has been described at step a). By analogy to what has been said hereinabove, this operation may be very generally effected by an inverse transformation in z or, in the case taken here by way of example, by an inverse Fourier transformation. The signal following transformation is shown on FIG. 12. If one designates by $TF^{-1}$ the inverse Fourier transformation, by $G_1(f)$ the logarithmic derivative and by $H(f)$ the frequency window, the signal of FIG. 12 may be expressed by the relation:

$$A(t) = TF^{-1}[G_1(f) \cdot H(f)]$$

f) The following step of the method consists in determining the envelope of the inverse transformation brought about in step e). This operation is effected by block 19 of FIG. 2 and appears as shown on FIG. 13. As is shown by this latter figure, the envelope exhibits a series of peaks 30, 31, 32, etc. of variable amplitude and spaced out in time. In order to arrive at this, one will advantageously employ the Hilbert transformation as described in the work "Probability, Random Variables and Stochastic Process" of A. Papoulis published by McGraw-Hill, 1984. If one designates by TH the Hilbert transformation, the envelope of FIG. 13 is expressed by:

$$\{[A(t)]^2 + [TH \cdot A(t)]^2\}^{\frac{1}{2}}$$

the value of A(t) being that obtained hereinabove.

g) From the envelope obtained in the preceding step, one determines the time spread $\Delta t$ separating the time origin from peak 30 exhibiting the greatest amplitude, which peak is due to the contribution from the periodic signal of the useful part defined hereinabove, in recalling that it is the periodic signal of the useful part in which are found the echoes sought after. Here the time origin is a relative origin which corresponds to the first echo. The interval $\Delta t$ as measured corresponds then very well to the interval separating the to echoes. This origin differs from that represented on FIG. 5. Such comes about from the fact that in employing the squared modulus calculated in step b) one loses the information which contains the time separating the time origin shown on FIG. 5 from the first echo.

In the special case, since the slope of the useful signal has been suppressed, the peak having the greatest amplitude due to the contribution of the periodic signal is indeed the first encountered and referenced 30, the distance e between the two faces 3 and 4 of the wall 2 of tube 1 being expressed by the relation $e = c \cdot \Delta t/2$. On the graph of FIG. 13, one measures $\Delta t = 0.2$ $\mu s$. If $c = 1.5$ mm/$\mu s$ as indicated hereinabove, one finds $e = 1.5 \cdot 0.2/2 = 0.15$ mm which corresponds well to the thickness of the tube which one knew from other means of measurement was equal to 0.15 mm.

Additional Considerations

The plastic tube employed hereinabove in order to explain the method of the invention gives well defined signals particularly due to the rigidity of the tube subjected to measurement. In numerous cases, the object for which the thickness is to be measured has no rigidity; furthermore, it is generally inaccessible and does not allow measurement by mechanical means. This is the case for instance of an artery in vivo for which one wishes to measure in a non-invasive manner the thickness of the wall.

Figure 14:
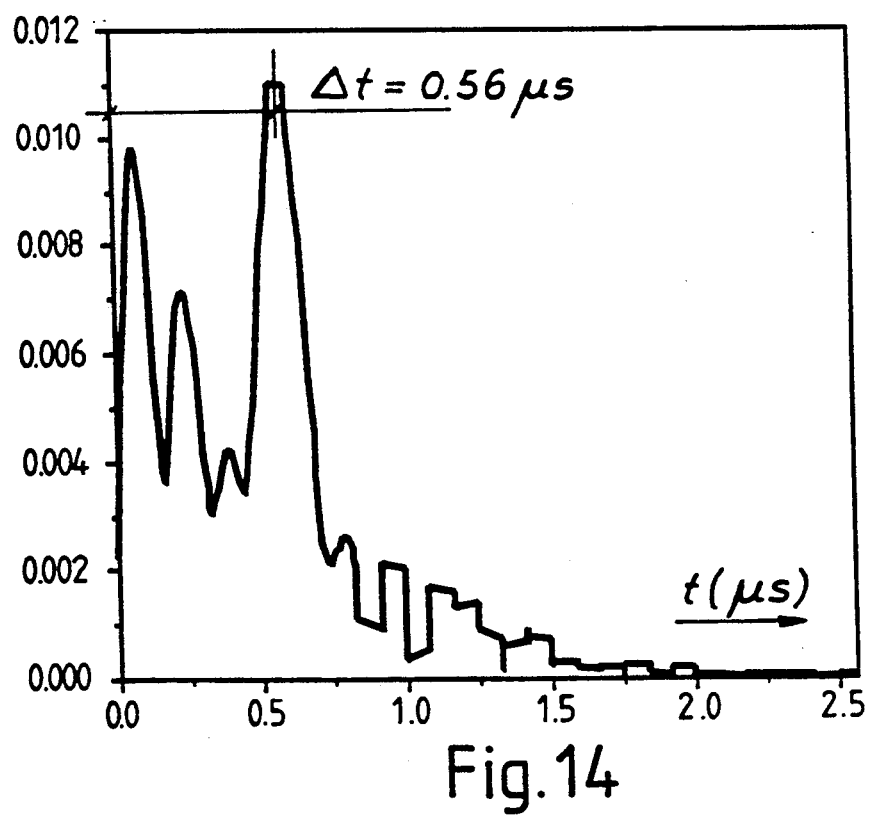
FIG. 14 shows the envelope diagram resulting from a similar measurement applied in vitro onto the artery of an animal.

FIG. 14 presents the signal envelope obtained in the next to last step of the method according to the invention from a swine femoral artery in vitro. In this case, there has been effected a slope correction as indicated hereinabove in step c). The envelope shows several peaks and without any contestation it is the peak of the greatest amplitude noted at 0.56 $\mu s$ which must be taken into consideration.

Figure 15:
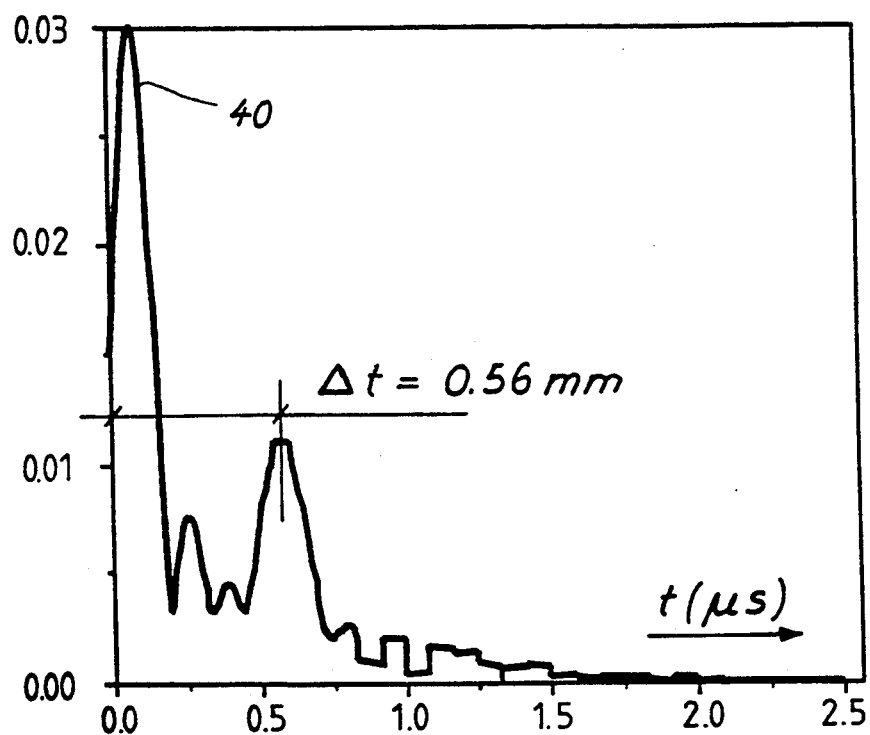
FIG. 15 is a diagram obtained under the same conditions as those of FIG. 14, but for which the step shown on FIG. 10 has not been carried out.

The diagram of FIG. 15 is an envelope obtained from the same artery but where the slope correction has not been effected. One readily finds at 0.56 $\mu s$ a peak corresponding to that sought after but this peak is preceded by another peak 40 of greater amplitude, such peak originating from the contribution of the linear part (or from the slope) of the useful signal which here is preponderant This teaching militates in favour of the systematic employment of the slope correction in all cases where the object to be measured shows little stability and/or is not accessible.

It has already been mentioned that the method may be employed for the measurement of the thickness of an artery. The same method may be profitably employed for measuring the interior diameter of the artery and generally for the measurement of any object exhibiting a thin layer for which one is concerned with measuring the thickness.

What we claim is:

1. A method for measuring the distance e separating two faces of an object which method comprises:

emitting an ultrasonic wave propagating at a velocity c toward the object;

detecting by a sensor echoes generated by reflection of said wave from the faces of said object, said sensor delivering a composite electrical signal g(t) having an amplitude varying as a function of time;

processing said composite electrical signal by the following sequence of steps:

a) transferring the composite electrical signal g(t) coming from the sensor into a frequency spectrum G(f) the amplitude of which is a function of the frequency, said spectrum exhibiting a real part Re (G(f)) and an imaginary part Im(G(f)), b) calculating the order n modulus of the frequency spectrum $|G(f)|^n = \{Re(G(f))^2 + Im(G(f))^2\}^{n/2}$, c) calculating the logarithmic derivative $(|G(f)|^n)'/|G(f)|^n$ of the modulus calculated in step b) in order to separate the existing echoes from the composite electrical signal, said logarithmic derivative exhibiting a useful part centered substantially on the frequency of the ultrasonic wave and a part having noise located on either side of the useful part, said useful part comprising a periodic signal onto which a substantially linear signal is superposed, d) applying a frequency window to the logarithmic derivative in order to isolate the useful part thereof and to eliminate the part having noise;

e) applying a transformation inverse to that of step a) at least to the periodic signal of said useful part, f) determining the envelope of the inverse transformation, said envelope exhibiting a series of variable amplitude peaks spaced out over time, g) determining the temporal speed $\Delta t$ separating the time origin from the peak showing the greatest amplitude due to the contribution of the periodic signal from the useful part, and h) determining the distance e separating the two faces of the object according to the relation $e = c \cdot \Delta t / 2$.

2. The method as set forth in claim 1 wherein said object is a thin layer and said faces define the thickness of the thin layer.

3. The method as set forth in claim 1 wherein step a) is preceded by a digitizing of the composite electrical signal, said digitizing being brought about by means of an analog-digital converter and the signal thus obtained being stored in a memory.

4. The method as set forth in claim 1 wherein the transformation effected in step a) is a Fourier transformation and the inverse transformation effected in step e) is an inverse Fourier transformation.

5. The method as set forth in claim 1 wherein the envelope appearing in step f) employs a Hilbert transformation of the signal appearing in step e).

6. The method as set forth in claim 1 wherein the frequency window appearing in step d) is a Hanning window.

7. The method as set forth in claim 1 wherein said object is an artery in a living being and said faces define the thickness of a wall of the artery.

8. The method as set forth in claim 1 wherein said object is an artery and said faces define the interior diameter of the artery.

9. The method as set forth in claim 1 wherein between step c) and step e) the substantially linear signal appearing at step c) is suppressed, the peak having the greatest amplitude as determined in step g) being then the greatest amplitude peak of the envelope obtained in step f).

10. The method as set forth in claim 9 wherein the useful part of the signal appearing at step c) is visualized and one proceeds to suppress the substantially linear signal by means of successive trials until a graphically satisfactory signal is obtained.

11. The method as set forth in claim 9 wherein suppression of the substantially linear signal is obtained by the following sequence of steps:

h) calculating from the expression of the order n modulus obtained in step b), for which one places $n=2$, the order 1 moment M1 and the order 2 moment m2, i) determining the line guided by $f = m1$ having as slope $p = k \cdot m2$, said line being expressed by the relation $p(f - m1)$ where f is equal to the frequency and k is a constant; and j) subtracting the line obtained in step i) from the logarithmic derivative obtained in step c).

12. The method as set forth in claim 9 wherein the substantially linear signal is suppressed by using the characteristics of said signal known a priori by a reference measurement.

13. The method as set forth in claim 9 wherein step a) is preceded by a step of digitizing the composite electrical signal, said digitizing being brought by means of an analog-digital converter and the signal thus obtained being stored in a memory.

14. The method as set forth in claim 9 wherein the transformation effected in step a) is a Fourier transformation and the inverse transformation effected in step e) is an inverse Fourier transformation.

15. The method as set forth in claim 9 wherein the envelope appearing in step f) employs a Hilbert transformation of the signal appearing in step e).

16. The method as set forth in claim 9 wherein the frequency window appearing in step d) is a Hanning window.

* * * * *